United States Patent [19]

Spilburg et al.

[11] Patent Number: 5,679,375

[45] Date of Patent: Oct. 21, 1997

[54] METHOD OF TREATING ULCERS WITH SULFATED POLYSACCHARIDES

[75] Inventors: Curtis A. Spilburg, Sunnyvale; Louis G. Lange, Potola Valley, both of Calif.; Esam Z. Dajani, Long Grove, Ill.

[73] Assignee: C.V. Therapeuctics, Palo Alto, Calif.

[21] Appl. No.: 481,751

[22] Filed: Jun. 7, 1995

[51] Int. Cl.$^6$ .............. A61K 9/14; A61K 9/20; A61K 9/48; A61K 31/715
[52] U.S. Cl. .............. 424/451; 424/455; 424/464; 424/489; 514/54
[58] Field of Search ............. 424/464, 451, 424/489, 455; 514/925, 926, 927, 54

[56] References Cited

U.S. PATENT DOCUMENTS

| | | | |
|---|---|---|---|
| 1,950,100 | 3/1934 | Crandall | 167/68 |
| 3,852,413 | 12/1974 | Cammarata | 424/1 |
| 3,903,270 | 9/1975 | Queuille | 424/195 |
| 3,951,949 | 4/1976 | Hamuro et al. | 260/999 |
| 4,511,559 | 4/1985 | Szendrei et al. | 514/54 |
| 4,581,221 | 4/1986 | Kuperus | 424/1.1 |
| 5,095,104 | 3/1992 | Gordon | 536/4.1 |
| 5,409,903 | 4/1995 | Polak | 514/23 |

OTHER PUBLICATIONS

Cook, D.L. et al., "Comparative Pharmacology and Chemistry of Synthetic Sulfated Polysaccharides," Arch. Inc. Pharmacodyn., 1963, 144 No. 1–2, pp. 1–19.

Prino, G. et al., "A Sulfate Glycopeptide (GLPS) as Inhibitor of Histamine Gastric and Duodenal Ulcers," Eur. J. Pharmacology, vol. 17, (1972), pp. 279–282.

Ranney, R.E. and Eich, S.J., "The Metabolism of Sodium Amylopectin Sulfate in the Rat," Toxicology and Appl. Pharmacology, vol. 15, pp. 593–603, (1969).

Landecker, K.D. et al., "Effect of Sodium Amylosulfate (Depepsen) on the Healing of Duodenal Ulcer," Gastroenterology, vol. 71, pp. 723–725, (1976).

Barnes, William et al, "A New and Potent Anitulcer Agent," Am. J. Surgery, v. 113, pp. 27–31, (1967).

G. Prino, et al., "Inhibition of Experimentally–Induced Gastric Ulcers in the Rat by a New Sulfated Glycopeptide," Eur. J. Pharmacology, vol. 15, (1971), pp. 119–126.

Bianchi, R.G. et al., "Antipeptic and Antiulcerogenic Properties of a Synthetic Sulfated Polysaccharide (SN–263)," vol. 47, No. 4, 1964, pp. 409–414.

Ellis, Cassius M. et al., "Effect of Protease Inhibitors on Experimental Peptic Ulceration," Tenth Annual Meeting of the Soc. for Surg. of the Alimentary Tract, 1969.

Takeuchi, Koji et al., "Influnce of Amylopectine Sulfate on Gastric Mucosa in Normal or Water–Immersion Stressed Rats," Japan J. Pharmacol. 26,506 (1976).

Okabe, Susumu et al., "Effects of An Antiulcer Drug, Sucralfate (A Basic Aluminum Salt of Sulfated Disaccharide), on Experimental Gastric Lesions and Gastric Secretion in Rats, " Digestive Dis. and Sci., vol. 28, No. 11 (1983).

McCarthy, Denis, "Sucralfate," New Mexico Regional Federal Medical Center, vol. 325, No. 14, pp. 1017–1025 Oct. 1991.

Cammarta, Peter et al., "Mechanism of the Antipeptic Action of Amylopectin Sulfate (SN–263), an Antiulcer, Mucin–Like Agent," Gastroenterology, vol. 61, No. 6, pp. 850–857, 1971.

Zimmon, D.S. and Mazzola, Vincent, "Amylopectin Sulphate (SN–263) Coats the Gastric Mucosal Surface," Gut, 1973, vol. 14, pp. 847–849.

(List continued on next page.)

*Primary Examiner*—Thurman K. Page
*Assistant Examiner*—James M. Spear
*Attorney, Agent, or Firm*—McDonnell Boehnen Hulbert & Berghoff

[57] ABSTRACT

This invention encompasses methods for inhibiting and/or treating gastric and duodenal ulcers by the administration of purified, high molecular weight sulfated polysaccharide compositions.

3 Claims, 3 Drawing Sheets

OTHER PUBLICATIONS

Kim, Young et al., "Studies on the Binding of Amylopectin Sulfate With Gastric Mucin," Gastroenterology, vol. 69, pp. 138–145, 1975.

Rees, W.D.W., "Mechanisms of Gastroduodenal Protection by Sucralfate," Am. J. Medicine, vol. 91, 2A–58S–2A63S Aug. 1991.

Rudick, Jack et al. "Effect of Low Molecular Weight Dextran on Gastric Ulceration and Gastric Secretion in Pylorus–Ligated Rats"(32799) Nov. 1967.

J. Watt and R. Marcus, "Ulcerative Colitis in Rabbits Fed Degraded Carrageenan," Letters to the Editor, J. Pharm. Pharmac., 1970, vol. 22, pp. 130–131.

Marcus, R. et al., "Ulcerative Disease of the colon in Laboratory Animals Induced By Pepsin Inhibitors," Gastroenterology, vol. 67, pp. 473–483, 1974.

Sun, David C.H. et al., "A Controlled Study on the Use of Propantheline and Amylopectin Sulfate (SN–263) for Recurrences in Duodenal Ulcer," Gastroenterology, vol. 58, No. 6, pp. 756–761 (1970).

Sun, David C.H., "A Controlled Trial of Antacid, Propantheline and Amylopectin Sulfate in Duodenal Ulcer," Am. J. Gastroenterology, vol. 60, No. 5 pp. 449–458, (1973).

Zimmon, David S. et al., "Specific Inhibition of Gastric Pepsin in the Treatment of Gastric Ulcer," Gastroenerology, vol. 56, pp. 19–23, (1969).

Cocking, J.B., "A Trial of Amylopectin Sulfate (SN–263) and Propantheline Bromide in the Long Term Treatment of Chronic Duodenal Ulcer," Gastroenterology, vol. 62, No. 1, pp. 6–10, (1972).

METHOD OF TREATING ULCERS WITH SULFATED POLYSACCHARIDES

BACKGROUND OF THE INVENTION

This invention relates to a method of treating or inhibiting ulcers in mammals.

The invention is based upon the discovery that sulfated polysaccharides may prevent the formation of gastric and duodenal ulcers or may be used to treat gastric and duodenal ulcers when orally administered in mammals. Many investigators have confirmed that sulfated polysaccharides and non-sulfated polysaccharides are effective in preventing experimental ulcers in animals. Hillyard et al., Proc Soc Exp Biol Med 115:1108–1112, (1964) shows this use with a non-sulfated polysaccharide, chitosan. The effectiveness of treating ulcers with sulfated glycopeptide is shown by Prino et al., Europ J Pharmacol 17:279–282 (1972) and Prino et al., Europ J Pharmacol 15:119–126 (1970). Dextran sulfate is shown to be effective in treating ulcers by Rudick et al. Proc Soc Exp Biol Med 127:781–783 (1968) and Barnes et al. Am J Surgery 113:27–31 (1967). Ellis et al. Am J Surgery 119:213–216 (1970) has shown the use of amylopectin sulfate for treating ulcers. An aluminum sult of sulfated disaccharide, sucralfate, has been shown to be effective as an anti-ulcer drug by Okabe et al. Dig Dis Sci 28:1034–1042 (1983).

Several mechanisms of the anti-ulcer action for sulfated polysaccharides have been reported in the medical literature. It appears that sulfated polysaccharides are excellent inhibitors of gastric protease activity according to Bianchi et al. Gastroenterology 47:409–414 (1964). In the early 1940's, Schiffrin et al. Am J Dig Dis 8:215–217 (1941) and Am J Dig Dis 9:205 (1942) demonstrated the dual role of acid and pepsin in a series of experiments. Isolated segments of the gastrointestinal tract of cats were perfused with either 0.1N HCl; aluminum hydroxyde gel and the acid pepsin solution; or aluminum hydroxyde gel alone. Acute ulcers were produced only in the acid-pepsin solutions. Cats with gastric fistulae were also used to show the effect of chronic acid and acid-pepsin administration. Three animals treated with only acid solutions for up to eight days developed no ulcerations. However, four animals treated with combined acid-pepsin solutions developed ulcerations in either the gastric or doudenal mucosa. These pioneering studies established that acid combined with pepsin is essensial for the induction of acute and chronic mucosal damage.

In the early 1970's, Gammarata et al. Gastroenterology 61:850–871 (1971) showed that in animals and Zimmon et al. Gut 14:847–849 (1973) showed in human studies that a sulfated polysaccharide, Depepsen, strongly binds with gastric mucins and with gastic mucosa. In theory, the binding with gastric mucins and with the mucosa could provide a barrier, acting in synergy with the mucus-bicarbonate layer of the stomach and doudenum.

There are possibly other mechanisms involved in the protective effects of sulfated polysaccharides. Rees Am J Med 91:2a–58s–2a–3s (1991) describes possible mechanisms of action for sucralfate which may not apply to all sulfated polysaccharides. These mechanisms include an effect on prostaglandins release, increased surface hydrophobicity and trapping of tissue growth hormones (EGF and FGF) at the mucosal surface.

Methods for preparing sulfated polysaccharides are also known in the art. For example, U.S. Pat. No. 3,624,069 describes the sulfation of cellulose with a sulfur trioxide/lower n-dialkyl amide sulfation complex. U.S. Pat. No. 4,480,091 describes a process for preparing cellulose sulfate esters in a three step process. Finally, U.S. Pat. No. 4,814,437 describes a method for preparing sulfated polysaccharides by subjecting the polysaccharide to a reducing step prior to sulfation.

A major concern for the development of a sulfated polysaccharide or an anti-ulcer agent relates to its toxicity and its tendancy for the induction of colitis. As reported by Watt et al. J Pharm Pharmacol 22:130–131 (1970) and in Gastroenterology 67:473–483 (1974) the induction of colitis has been associated with many sulfated polysaccharides. It is speculated that incidental colitis may be a consequence of the high inorganic sulfate content in the sulfated polysaccharides. There is a need for a safe, effective high molecular weight, high purity, essenctially non-absorbable and non-degradable sulfated polysaccharide for the prevention and/or treatment treatment of gastric and duodenal ulcers.

SUMMARY OF THE INVENTION

The present invention is directed to a method for treating or preventing gastric and/or duodenal ulcers by high molecular weight 3-sulfated polysaccharides that are essentially non-absorbable and nondegradable in the alimentary tract. The polysaccharide compound of the present invention has greater than 95% of its molecular weight greater than 75,000 Daltons; the sulfate to monomer ratio is between 1.0 and 3.0; it has less than 0.5% by weight of the material is free sulfate; it has been found to be effective in treating gastric ulcers. The high molecular weight sulfated polysaccharides of this invention can be administered to humans in tablet form, or by any other pharmaceutically acceptable method that inhibits or treats gastric and duodenal ulcers.

DESCRIPTION OF THE PREFERRED EMBODIMENT

The present invention is a non-obvious improvement over the prior art of this invention, because the very high molecular weight sulfated polysaccharides are potent inhibitors of gastric ulcer formation, non-absorbable from the gastro-intestinal tract, move continuously in contact with the gastro-intestinal tract and are essentially non-toxic. Therefore, the very high molecular weight sulfated polysacharieds of the present invention may be used to prevent and/or treat gastric and duodenal ulcers.

The exact mechanism of the anti-ulcer activity of the very high molecular weight polysaccharides is unknown. As previously discussed, possible mechanisms of action for sulfated polysaccharides include the well documented antipeptic activity, the binding of growth hormones to insure their ability for the induction of ulcer healing, binding to the gastric duodenal mucosai from gastric acid to allow tissue repair and the slowing of acid diffusion at the epithelial cell level, in effect acting as substitute mucus.

The very high molecular weight sulfated polysaccharides may function in all of the forgoing actions, however it is believed that they may serve as a weak anti-bacterial agent and may even potentiate the effects of antibiotics such as clarithromycin and ampicillin to act against *Helicobacter pylori*. The sulfated polysaccharides of the present invention may detach *H. pylori* from the gastric muscosa so it can be readily attacked by an antibiotic. This action most likely occurs as the sulfated polysaccharide binds to the gastric mucosa.

The cytoprotective effect of the sulfated polysaccharides of the present invention, as demonstrated against the absolute ethanol induced gastric injury test of Example 7 should protect the gastroduodenal mucosa against the damaging effects of ammonia and other injurious substances produced by *H. pylori*.

The very high molecular weight sulfated polysaccharides of the present invention are distinguished from the prior art sulfated polysaccharides in that they are highly purified, possess a very high molecular weight and are non-toxic.

Further, the compounds of the present invention, having very high molecular weight, possess a relatively large molecular size that aids in their passage through the gastrointestinal tract without being absorbed.

Free sulfate and low molecular weight sulfated polysaccharides are undesirable byproducts of the manufacture of very high molecular weight sulfated polysaccharides. In fact, the presence of toxic, low molecular weight sulfated polysaccharides or inorganic sulfate in high molecular weight sulfated polysaccharide compositions obviated their use as an ingestible drug for any purpose. Therefore, the very high molecular weight sulfated polysaccharide of polysaccharide of this invention must include less than 0.5 wt % and preferably 0.25 wt % to 0.1 wt % free sulfate and moreover, it must contain less than 5% by weight of sulfated material having a molecular weight less than 75,000 Daltons. Typically, it will be essentially free of low molecular weight sulfated materials and inorganic sulfates and will have a molecular weight of at least about 500,000 Daltons and an average molecular weight greater than 2,000,000 Daltons. The high molecular weight sulfated polysaccharides of this invention will have a sulfate to monomer ratio of from 1.0 to 3.0, preferably 2.0.

We have found a method to utilize the very high molecular weight sulfated polysaccharides, free of toxic low molecular weight polysaccharides and free of sulfate byproducts. The very high molecular weight sulfated polysaccharide is extremely useful in preventing and treating of gastric and duodenal ulcers.

The very high molecular weight sulfated polysaccharides of this invention are characterized as follows:

| Property | |
|---|---|
| Appearance | Off-White Powder |
| Sodium content | 11.0–15.0 wt % |
| Carbon content | 14.0–17.0 wt % |
| Hydrogen content | 2–3.5 wt % |
| Nitrogen content | <0.5 wt % |
| Sulfur content | 16.0–19.0 wt % |
| Degree of sulfation | 2 ± 1.0 |
| % Free Sulfate | <0.50% |
| Viscosity | >4000 centipoise |
| pH on dissolution | 6–9 |
| Wt. % with Molecular Wt. >75,000 | >95% |
| Average Molecular Wt. | >500,000 Daltons |

Very high molecular weight sulfated polysaccharides of this invention are made by the following steps: (1) prepare an anhydrous DMF suspension of a high molecular weight polysaccharide or cellulose from a source such as cotton linters; (2) mix the anhydrous DMF suspension of high molecular weight polysaccharides or cellulose with a sulfur source such as a sulfur trioxide/DMF complex; (3) neutralize the acidic mixture after the sulfation reaction is essentially complete to give a crude sulfated polysaccharide mixture including crude sulfated polysaccharides and aqueous reactants; (4) separate crude, very high molecular weight sulfated polysaccharides from the aqueous crude sulfated polysaccharide mixture; (5) wash the separated crude very high molecular weight sulfated polysaccharides; and (6) dry the resulting crude intermediate product.

The dried crude intermediate product is then purified to exclude essentially all impurities such as free sulfates and sulfated polysaccharides having a molecular weight less than 75,000 Daltons. Purification is preferably accomplished by dissolving the dried crude intermediate product in water to form an aqueous crude solution containing very high molecular weight sulfated polysaccharides and impurities including free sulfate and low molecular weight sulfated products having molecular weights less than 75,000 Daltons. The crude aqueous solution is subjected to a first filtration step to produce a very high molecular weight sulfated polysaccharide containing filtrate essentially free of unreacted polysaccharides and/or fines. Preferably the first filtration step consists of at least two successive filtration steps; the first across a 5 micron filter and the next across a smaller filter and so forth until the final filtration step which preferably uses a 1 micron filter.

The filtrate produced in the first filtration step is then diafiltered in a second filtration step with a 500,000 Dalton molecular weight cut-off membrane against deionized water to produce a purified very high molecular weight sulfated polysaccharide product. The diafiltration step eliminates free sulfates, bicarbonate, and essentially eliminates low molecular weight sulfated polysaccharides having molecular weights less than 75,000 Daltons that remain in the filtrate from the first filtration step. The aqueous purified product is preferably dried before it is used. Any drying process known in the art, such as spray drying, drum drying, fluid bed granulation, or lyophilization, that is capable of producing powder from an aqueous solution containing dissolved solids may be used.

Accordingly, the present invention includes very high molecular weight sulfated polysaccharide compounds of the formula:

The chemical formula for a monomeric unit is $C_6H_8Na_2O_{11}S_2$, wherein n is 1400 or greater and wherein R is $-SO_3Na$.

Cellulose sulfate is preferably used in preparing a very high molecular weight sulfated polysaccharide of this invention which is manufactured in three basic steps: (1) sulfation of chemically pure cellulose using sulfur trioxide in dimethyl formamide; (2) filtration to remove water insoluble contaminants and diafiltration against 500,000 Dalton molecular weight or greater cut-off membranes to remove potentially toxic small molecular weight contaminants; and (3) an optional formulation step to produce a tablet, capsule, liquid or foodstuff comprising a very high molecular weight sulfated polysaccharide for human consumption.

The very high molecular weight sulfated polysaccharides of this invention are administered to humans in doses in amounts effective to inhibit or treat gastric, peptic or duodenal ulcers, preferably in amounts ranging from about 10 mg. to about 5,000 mg. Preferably, the amounts may range from about 250 mg. to about 1000 mg.

A preferred very high molecular weight sulfated polysaccharide of this invention is cellulose sulfate consisting of chemically pure cotton cellulose linters which have been sulfated in a preferred ratio of about two moles of sulfate per mole of monomer. Cotton linter is a preferred source of cellulose since it is the most chemically pure form of commercial cellulose yet discovered. Cotton linter consists of glucose units polymerized to a total of about 14,000 monomer units with a molecular weight of about 2.4 million.

Naturally occurring very high molecular weight polysaccharides and preferably cellulose polymers, often regarded as waste, can be converted into a highly potent, cheap, non-absorbed, non-toxic, and nondegradable inhibitors of ulcers that can be administered as soluble agents in small and well-tolerated quantities.

The very high molecular weight sulfated polysaccharide inhibitors of gastric and duodenal ulcers can be administered in various pharmaceutical dosage forms such as tablets, capsules, liquids and powders, alone or in the presence of one or more pharmaceutical excipient such as surfactants, flavoring agents, coloring agents, starch, sugars and the like excipients. The very high molecular weight sulfated polysaccharides of this invention can also be incorporated into food products. Those skilled in the food and pharmaceutical arts will recognize a wide variety of formulations and vehicles for administering sulfated polysaccharides.

The invention is illustrated further by the following examples which are not to be construed as limiting the invention in scope or spirit to the specific procedures described in them.

EXAMPLE 1

This example details a method for manufacturing a very high molecular weight sulfated polysaccharide of this invention that is useful in inhibiting and/or treating gastric ulcers.

A purified very high molecular weight sulfated polysaccharide is prepared by sulfating cellulose using sulfur trioxide dimethylformamide (DMF/SO$_3$) complex in anhydrous dimethylformamide (DMF) solvent according to the following method.

A. Dried cotton linters (8.75 kg) were shredded using a commercial paper shredder and soaked in 208 liters of dry DMF under a blanket of nitrogen. The mixture was cooled to 8°–10° C.

B. After 3 hours, 33 kg of DMF/SO$_3$ complex were added with stirring. The reaction temperature was maintained between 15° C. and 20° C. for 150 min.

C. Solid sodium bicarbonate (51 kg) was added to the combined mixture and allowed to mix for 10 minutes to neutralize any excess acid. This was followed by 15L of deionized water. Finally, acetone was added (95L) and the mixture stirred overnight.

D. The next day, the reaction mixture was spun in a centrifuge, and the solid collected and resuspended in 208L of acetone. The resuspended mixture was spun again in the centrifuge.

E. The solid recovered from the centrifugations was dried on a drying table overnight.

F. The crude dried sulfated polysaccharide was dissolved in water (600–1000L) so the solution was about 0.5–1.0 wt % solids.

G. The mixture was sequentially filtered using a 50 micron, 5 micron, and 1 micron filter. A diafiltration apparatus equipped with 500,000 Dalton molecular weight cut-off membranes (Koch Membranes, pm 500A) was then used to diafilter the 1 micron filtrate against deionized water to an effluent conductivity of <300 mS/cm.

H. The diafiltered solution was dried (in a spray drier or drum drier) and the resulting very high molecular weight sulfated polysaccharide of this invention was collected in containers of appropriate size for storage and shipment.

The very high molecular weight sulfated polysaccharides exhibited the following properties (the average values for nine manufacturing runs):

TABLE I

| Property | Result |
| --- | --- |
| Appearance | Off White |
| Specific Rotation of Hydrolysate | 16.4° |
| Degree of Sulfation | 2.06 |
| % Free Sulfate | 0.18% |
| Dimethylformamide | 18 ppm |
| Molecular Wt. | 3,800,000 Daltons |
| % Low Molecular Weight Sulfated Cellulose | 0.67% |

EXAMPLE 2

Nuclear magnetic resonance (NMR) spectroscopy is the standard method for structural analysis of organic molecules. While this technique is widely used for structure elucidation of small molecules, there are several problems which make this method of limited usefulness for large molecules, such as the very high molecular weight sulfated polysaccharides of this invention.

$^{13}$C NMR Spectra

Figure 1:
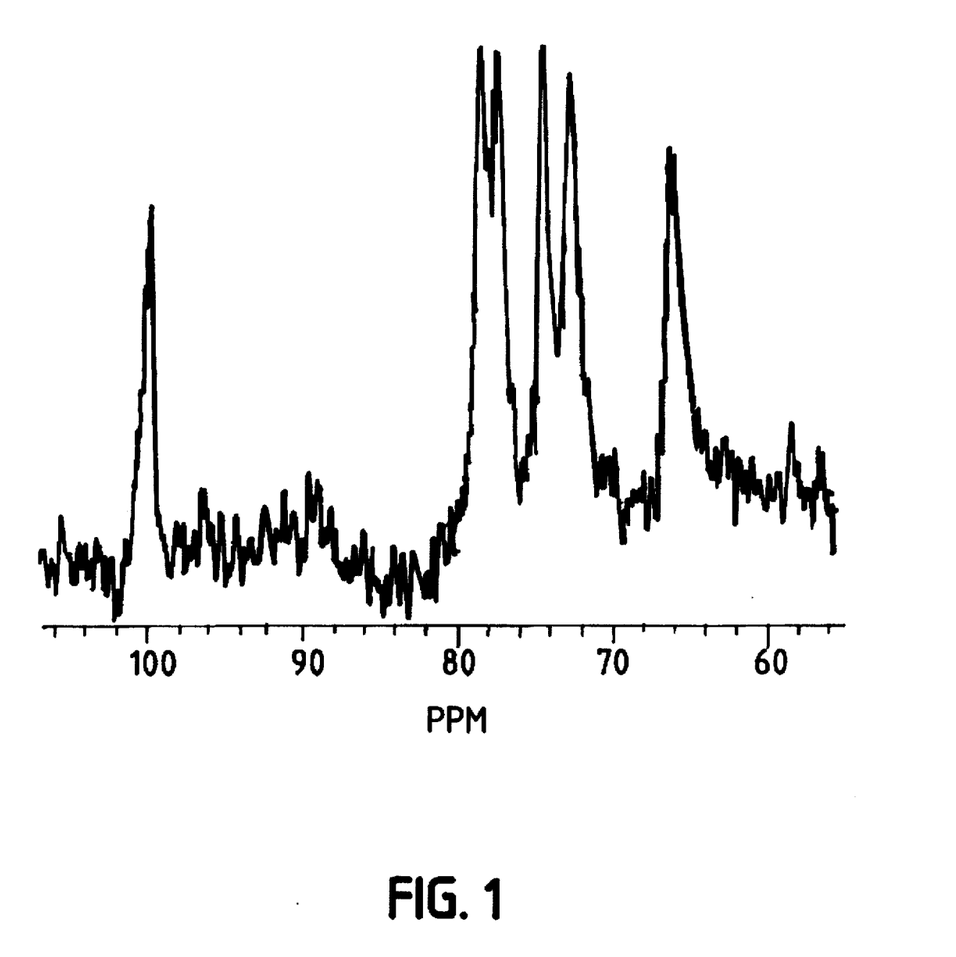
FIG. 1 is a $^{13}$CNMR spectrum of a very high molecular weight sulfated polysaccharide of this invention.
Figure 2:
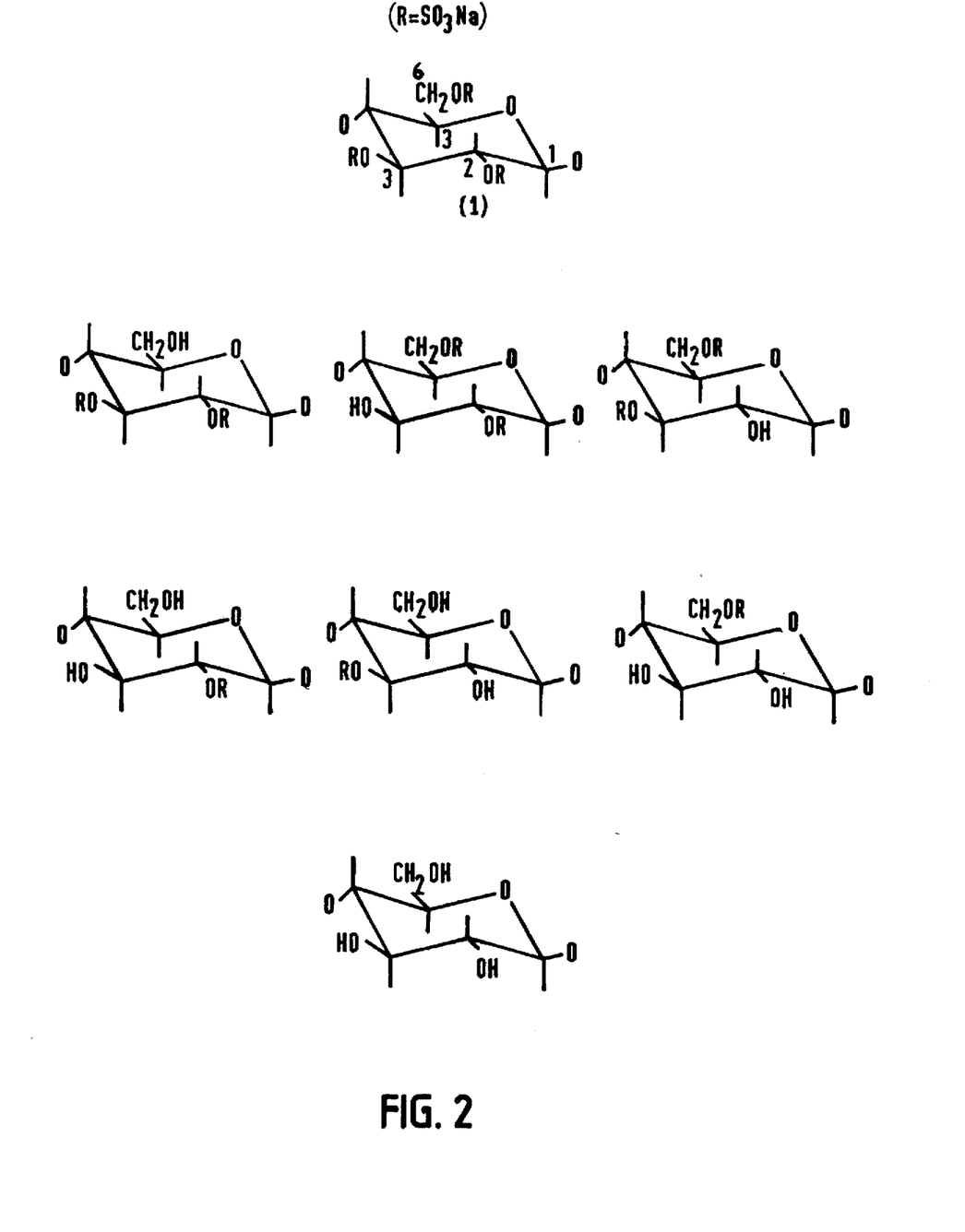
FIG. 2 shows the possible structures of sulfated cellulose of this invention.

The $^{13}$C spectrum (90 MHz) of a very high molecular weight sulfated polysaccharide produced by the method of Example 1 is shown in FIG. 1. The eight different structural possibilities for any given saccharide of the very high molecular weight sulfated polysaccharides should give rise to 48 signals. (FIG. 2). However, since the observed spectrum produces only six well-defined signals, there is much overlap, making definitive assignments for all the carbon atoms impossible. The position and intensity of these various resonances are summarized below for the compound of Example 1.

TABLE II

| $^{13}$C NMR CHEMICAL SHIFTS | |
| --- | --- |
| CHEMICAL SHIFT, ppm | INTEGRATED INTENSITY |
| 100.2 | 10.00 |
| 75.8,77.4 | 29.39 |
| 74.4,72.5 | 33.00 |
| 66.0 | 14.85 |

Even though some assignments are controversial, See Kamide, K. and Okajima, K. (1981) *Polymer Journal* p. 163–166 and Kowasaka, K. Okajima, K. and Kamide, K. (1991) *Polymer Journal*, p. 823–836, from studies on model compounds, there is agreement on the spectroscopic behavior of carbon 1 and carbon 6. For example, in going from β-D-glucopyranose to the corresponding 6-sulfate derivative, signals at these two positions shift in a characteristic way. From data on this model compound, it can be predicted with confidence that the chemical shift at 100.2 ppm observed in the analyzed compound is most likely due to carbon 1. Moreover, in the starting unsubstituted saccharide there is a resonance that is shifted by 6.6 ppm in the sulfated derivative. Taken together, this indicates that the resonance in native cellulose which occurs at 60.5 ppm and is shifted to 66.0 ppm on sulfation is due to carbon 6. Based on this, it may be concluded that the very high molecular weight compound analyzed is totally sulfated at position 6 since there is no evidence of a signal at around 60.5 ppm. This is also verified by the integrated intensity (14.85) of this signal, which corresponds to only one carbon atom. If the integrated intensities at 72.5 ppm, 74.4 ppm, 77.4 ppm, and 78.5 ppm are summed, the total (62.4) is about four times that from carbon 6. This indicates that these signals are derived from carbons 2, 3, 4 and 5 in the various mono-, di-, tri- and unsubstituted forms. Finally, the signal at 100.2 ppm from carbon 1, which is only ⅔ the intensity of the others has a lower value because of a longer relaxation time.

Since carbon 6 is sulfated in all the anhydro glucopyranose units, the number of contributing structures to the $^{13}C$ NMR spectrum is diminished. It is also believed that the resonances from carbon 1 and sulfated carbon 6 are the same in all contributing structures, (See Kowansaka, K. Okajima, K. and Kamide, K. (1991) *Polymer Journal*, p. 823–836), reducing the number of magnetically non-equivalent carbons from 48 to 16. Since there are only 4 resonances to account for in the remaining 16 structures, it is still not possible to determine the relative proportions of sulfation at carbons 2 and 3.

To summarize, it is clear that carbon 6 is, within the limits of this analysis, totally sulfated. Since the polysaccharide contains more than one sulfate per monomer, the other sulfate is distributed between carbons 2 and 3.

EXAMPLE 3

This example describes methods for characterizing the very high molecular weight sulfated polysaccharides of this invention.

Determination of Degree of Substitution

Dowex-50W ion-exchange resin ($H^+$ form, dry mesh 200–400; 8% cross linkage) was added with gentle swirling to a 100 ml beaker containing 50 ml of deionized water. The water was removed and the procedure was repeated two more times. The resin was added to a 1.0×20 cm column to a bed height of 18 cm, and the column was washed with 25 ml of deionized water using a peristaltic pump at a flow rate of 30 ml/hr.

A 1.0 mg/ml solution (15 ml) of a very high molecular weight sulfated polysaccharide in water was pumped onto the resin and 5 minute fractions were collected. When all of the sample was applied to the resin, the pH of each fraction was measured with a calibrated pH electrode. Those fractions with a pH less than or equal to 3.5 contained protonated sulfated polysaccharides and were pooled in a 50 ml glass beaker.

A rinsed conductivity electrode was immersed in the beaker containing the protonated sulfated polysaccharide and the initial conductivity reading was recorded. The solution was titrated by recording the conductivity after each addition of 100 μl of 0.1N NaOH. As base was added, the conductivity decreased until the equivalence point was reached, then the conductivity increased. The equivalence point was determined by drawing a straight line through the descending data points and a straight line through the ascending data points. The intersection point of the two lines is the equivalence point, expressed as mls of 0.10N NaOH.

After completion of the titration, the amount of sulfated polysaccharide present was determined spectrophotometrically using Toluidine Blue. In detail, 200 μl of sulfated polysaccharide solutions, ranging in concentration from 2.5 μg/ml to 40 μg/ml, were pipetted into test tubes. A blank was prepared which contained only 200 μl of water, and various aliquots were removed from the titration and the volume was adjusted to 200 μl by adding an appropriate volume of water. After adding 10 μl of 1 mg/ml Tohidine Blue to each tube, the absorbance was read at 540 nm, after zeroing against the blank. A standard curve was prepared and the amount of sulfated polysaccharide in a sample was determined from the linear portion of the curve. Using this value and the equivalence point, the % sulfate can be determined from the following relation:

$$\%SO_3 = \frac{(8 \times \text{mls NaOH equivalence pt.})}{(\text{mg sulf. polysaccharide toluidine blue assay})}$$

The degree of substitution is defined as the number of hydroxyl groups on the polysaccharide that have been replaced by the $OSO_3H$ functional group. Every OH group which is lost is replaced by an $OSO_3H$ group, increasing the molecular weight by 80. Since the molecular weight of a starting cellulose monomer is 161, the molecular weight (MW) increases according to the following relation, where x=degree of the substitution:

$$MW=161+80x$$

As sulfate is introduced into the polymer its percentage (y) changes according to the following relation:

$$y=80x/(161+80x)$$

When this equation is solved for x, the degree of substitution can be calculated from the percent $SO_3$ in the sample.

$$x=161y/80(1-y)$$

Molecular Weight Determination

The molecular weight profile of a very high molecular weight sulfated polysaccharide is determined by aqueous gel permeation chromatography using a glucose-polydivinyl benzene GPC-HPLC column. Since the sulfated polysaccharide of this invention has a very high molecular weight and viscosity, the column is run at elevated temperatures to lower the viscosity to prevent pressure problems. Importantly, columns of this type can be calibrated using standards of known molecular weight, allowing the molecular weight of an unknown sample to be determined by comparing its elution volume to those of samples of known molecular weight. This HPLC assay is used to determine the molecular weight range of a high molecular weight sulfated polysaccharide and a cumulative weight fraction plot is used to calculate the percentage low molecular weight compounds.

A mobile phase solution was prepared by adding 200 ml of DMSO to 800 ml of 0.1M NaOH and then the solution was filtered through a 0.2 μm filter. Molecular weight standard solutions were prepared by dissolving individual molecular weight standards in mobile phase solution to yield a concentration of 1 mg/ml. Finally, a sample solution of a very high molecular weight sulfated polysaccharide was prepared by dissolving the sulfated polysaccharide in the mobile phase solution to yield a concentration of 1 mg/ml. The samples were analyzed by injecting 500 µl of each individual standard in descending order of molecular weight value and then injecting 500 µl of the sample solution. The column was operated at 80° C.

A standard curve was prepared by plotting $\log_{10}$ ($M_p$) of the standards with known molecular weight versus their elution time. The equation describing the standard curve was calculated by the method of least squares. The $\log_{10}$ ($M_p$) of the sulfated polysaccharide sample was then determined from its elution time and the derived equation.

The percentage of low molecular weight sulfated compounds is calculated using the following equation:

% Low Molecular Weight=(AUC$_{small}$/AUC$_{total}$) * 100

Where:

AUC$_{total}$=integration of the total area under the curve of the sample peak.

AUC$_{small}$=integration of the area under the curve of the sample peak from the elution time of the 75,000 Daltons standard to the end of the curve.

EXAMPLE 4

Infra-red spectroscopy is used to verify the presence of sulfated groups in the very high molecular weight sulfated polysaccharides prepared by this invention. This example details the method to produce a Fourier transform infrared (FTIR) spectrum of very high molecular weight sulfated polysaccharides prepared by the methods of this invention.

A sulfated polysaccharide/potassium bromide sample pellet was prepared by adding approximately 5 mg of solid sulfated polysaccharide and 495 mg of oven dried KBr into a polystyrene vial containing one plexiglass ball. The solids were mixed with a Wig-L-Bug (International Crystal Laboratories), and 200 mg were loaded into a pellet die. A clear pellet was prepared by subjecting the evacuated die to 6 metric tons of pressure for 10 minutes. The clear pellet was removed from the die and placed in the FTIR sample chamber.

Figure 3:
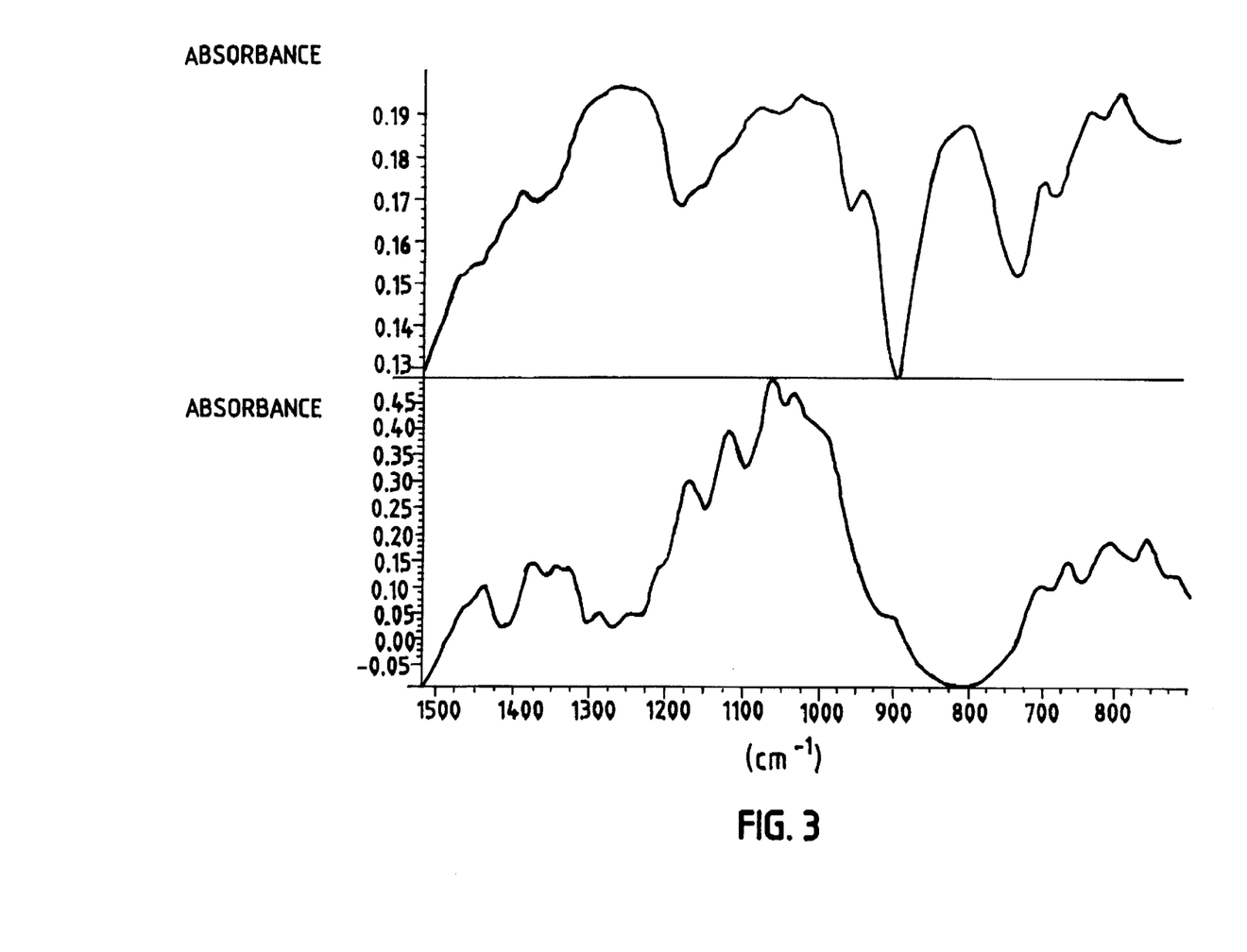
FIG. 3 is a FITR spectrum of a very high molecular weight sulfated polysaccharide of this invention.

The sample spectrum, (FIG. 3), can be visually inspected to verify the presence of certain characteristic absorptions. At about 800 cm$^{-1}$ there is a distinct peak due to C-O-S stretching and at about 1240 cm$^{-1}$ there is a distinct peak due to the S=O bond stretch. A reference spectrum of cotton linter, (FIG. 3, bottom), shows the presence of these new bonds due to the sulfate group.

EXAMPLE 5

In order for the very high molecular weight sulfated polysaccharides of this invention to inhibit and/or treat gastric ulcers, they must be viable in the stomach where they can experience pH values less than 2.0. Since cellulose based compounds are less stable at acid pH, this investigation was carried out to demonstrate that degradation and loss in potency did not occur to a significant degree under simulated gastric conditions.

A 1.0 mg/ml solution of a very high molecular weight sulfated polysaccharide was prepared in a simulated gastric fluid (7 ml concentrated HCl, 3800 units pepsin and 2 g NaCl in 1L of water), and a 1.5 µl aliquot was removed for analysis. The molecular weight of the aliquot was determined (Example 3). The remaining solution was placed in a 37° C. water bath, and time 0 was recorded as the test tube was placed in the bath. At 1 hr, 2 hr, and 25 hr, aliquots were removed and analyzed for potency, molecular weight and the percent with a molecular weight less than 75,000 Daltons. As shown in Table III, over a two hour incubation period, there is little change in molecular weight. While the starting molecular weight was 5,000,000 Daltons, there is large error at these high values so there is probably no significant difference between this value and the values seen at 1 hr and 2 hr, 3,900,000 Daltons and 3,600,000 Daltons, respectively. However, after 25 hr, there is evidence of degradation with the molecular weight decreasing to 850,000 Daltons.

Another measure of degradation is the percentage of carbohydrate which appears below an arbitrary molecular weight. In this case, 75,000 Daltons was chosen since this is understood as the value above which no absorption occurs. As shown in Table III, after 2 hr, only about 1% of the sample is degraded to a molecular weight below this value, and even after 25 hr, this value has increased to only 3.4%.

TABLE V

STABILITY WITH PEPSIN AT pH 1.5 AND 37° C.

| TIME (hrs) | Molecular Wt. (kDa) | % > 75 kDa |
| --- | --- | --- |
| 0 | 5000 | 0.0 |
| 1 | 3900 | 0.4 |
| 2 | 3600 | 1.1 |
| 25 | 850 | 3.4 |

Taken together, this example indicates that over the residence times commonly occurring in the stomach, the very high molecular weight sulfated polysaccharides of this invention are minimally degraded.

EXAMPLE 6

The objective of this study was to determine the amount of absorption of orally administered [$^{14}$C]-labeled, very high molecular weight sulfated polysaccharides in male rats. The [$^{14}$C]-labeled cellulose used in this study was isolated from cotton bolls which had been exposed to $^{14}CO_2$, and the polysaccharide was sulfated following the procedure given in Example 1.

Six male Sprague-Dawley rats were given a single 375 mg/kg dose of sulfated [$^{14}$C]-labeled cellulose by oral gavage (Table VI).

TABLE VI

| DOSE SOLUTION ANALYSIS | |
| --- | --- |
| Parent Compound (mg/ml) | 25.0 |
| Radioactivity (DPM/ml) | 412898 |
| Radioactivity (µCi/ml) | 0.186 |
| Activity (DPM/mg) | 16516 |
| Total Dose Administered (mg) | 110 |

Following dose administration, animals were placed in Elizabethan collars and fitted with fecal cups to prevent fecal contamination of collected urine. Cumulative urine samples were collected from 0–4, 4–8, and 8–24 hours post-dose. Feces were removed from the fetal cups at 12 hours and 24 hours post-dose. Serial blood samples were obtained at 0.33, 1, 3, 6, 10, and 24 hours following dose administration. In addition, a thorough cage-wash was performed following the last sample collection. Derived plasma, urine, cage wash, fetes and dose solution were assayed for radioactive content by oxidation followed by scintillation counting. The results were used to assess the oral absorption of radioactivity following single oral dose administration of high molecular weight sulfated [$^{14}$C]-cellulose.

Radioactivity levels were not detectable in any of the plasma, urine and cage wash samples collected during the study. From the amount of radioactivity administered and the detection limit of the method, in this study, greater than 99.5% of the very high molecular weight sulfated polysaccharide was not absorbed.

EXAMPLE 7

The purpose of this example is to characterize the gastric antisecretory and antiulcer activity of the compound of the present invention (hereinafter known as CVT-1). Four standard laboratory tests of antisecretory/antiulcer action in the rat are used. Evaluation in each test model is performed as a separate experiment. The models are:

1. Four Hour Pylorus-Ligated Rat (volume, acidity, protease activity)
2. Eighteen Hour Pylorus-Ligated Rat (lethality, ulcer index)
3. Ethanol-induced Gastric Injury (ulcer index)
4. Aspirin-induced Gastric Ulcers (ulcer index)

The test includes studies with CVT-1 at a dose-level of 125 mg/kg.

Each experiment included a total of three treatment groups: CVT-1 125 mg/kg, plus two control groups viz. saline 10 ml/kg or sucralfate 125 mg/kg. Each treatment was tested in 12 to 15 rats. CVT-1 was dissolved in warm water; sucralfate was suspended in warm water with the addition of 0.01 percent Tween 80. Solutions and suspensions were always freshly prepared immediately prior to use. Treatments were always administered by gavage. Treatment dose volumes were always 10 ml/kg. In all the experiments, male rats of the Charles River Crl:CovsCD(SD)BR strain were utilized. The male rats were at the ages of 9–13 weeks at the start of the study. Each of the studies described would utilize a single intragastric administration of CVT-1, the reference standard sucralfate, if applicable, and saline (placebo).

Results of the study revealed that CVT-1, at the dose-level of 125 mg/kg, was definintely active in 3 of the 4 models in which it was tested. CVT-1: (1) reduced acidity and proteolytic activity of gastric juice in the 4 hour pylorus-ligated rat; (2) reduced ulcer severity and mortality in the 18 hour pylorus-ligated rat, and (3) reduced ulcer severity in the ethanol-induced gastric injury model. CVT-1 revealed no appreciable activity in the aspirin-induced gastric ulcer model because of a low level of the dose of CVT-1. It is anticipated that at higher dose levels, activity will be shown in the aspirin-induced gastric model.

(A) Four Hour Pylorus-Ligated Rat

After a 24 hour fast, rats were lightly anesthetized by methoxyflurane inhalation, and the standard Shay procedure (Shay et al. Gastroenterology 5:43, 1945) for ligation of the pylorus was performed. Immediately after pyloric ligation, rats were dosed by gavage with saline (control), CVT-1 125 mg/kg, or sucralfate 125 mg/kg; dose volumes 10 ml/kg.

Four hours after pyloric ligation, rats were sacrificed, stomachs were removed and gastric contents were saved for analysis.

For each rat, the pH and volume (ml/4 hr) of gastric secretion were measured and recorded. Acidity was determined by titrating a 1.00 ml aliquot to pH 7.00 with 0.1000N sodium hydroxide. Total acid output (TAO) was calculated by the formula:

$$TAO = Volume \times Acid\ Concentration$$
$$(meq/4hr)\quad (ml/4hr)\quad (meq/L).$$

For rats treated with CVT-1, or saline, the pepsin concentrations (i.e. total protease) of the gastric juice also were measured. Bovine hemoglobin (2.0 percent) was used as the substrate. Diluted aliquots of gastric juice were incubated with 5.0 ml substrated at pH 2.00 and 37.0° C. for 10.0 minutes. Reaction was stopped by the addition of 10.0 ml of 5.0 percent trichloracetic acid. (For blanks, the trichloracetic acid was added before beginning the incubation.) Reaction mixtures were filtered through Whatman #3 filter paper. The optical densities of the filtrates at 280 nanometers were measured by spectrophotometer against distilled water, blank corrected, and compared to the standard pepsin curve. Total pepsin output (TPO) was calculated by the formula:

$$TPO = Volume \times Pepsin\ Concentration$$
$$(\mu g/4hr)\quad (ml/4hr)\quad (\mu g/ml).$$

Results are presented as means±standard errors of the means (n=12 per group). Statistical significance of differences between means were determined by analysis of variance and Newman-Keuls multiple comparisons test.

TABLE 7A

INFLUENCE OF CVT-1 UPON GASTRIC SECRETION IN THE 4 HOUR PYLORUS-LIGATED RAT

| Treatment | Volume (ml) | Gastric (pH) | Titratable Acidity (mEq/L) | Total Acid Output (μEq/4 hr) | Pepsin Conc. (ug/ml) | Total Pepsin Output (ug/4 hr) |
|---|---|---|---|---|---|---|
| Saline (control) | | | | | | |
| mean | 7.2 | 1.2 | 89.2 | 651.5 | 1582.1 | 10656.5 |
| sem | 1.0 | 0.0 | 3.3 | 90.5 | 115.2 | 1018.4 |
| CVT-1 | | | | | | |
| mean | 5.7 | 1.4 | 74.8* | 455.3 | 381.4* | 2072.1* |
| sem | 0.7 | 0.1 | 6.5 | 77.1 | 39.3 | 251.3 |
| reduction (%) | 20.6 | −11.4 | 16.2 | 30.1 | 75.9 | 80.6 |
| Sucralfate | | | | | | |
| mean | 7.3 | 1.4 | 95.3 | 681.8 | Not tested | |
| sem | 0.7 | 0.1 | 4.7 | 56.9 | | |
| reduction (%) | −0.1 | −16.1 | −6.9 | −4.7 | | |

*significantly different from saline control, p < 0.05

For the 12 saline treated rats, mean volume of gastric secretion was 7.2±1.0 milliliters, mean pH of gastric juice was about 1.2, mean titratable acidity about 89 meq/L, and mean total acid output (TAO) was about 651 μEq/4 hr (Table 7A).

Compared to saline control, values of the rats in the CVT-1 treated group were reduced by about 15 to 30 percent; the reduction of titratable acidity was statistically significant (although not very appreciable in size: 16.2 percent). For the rats in the sucralfate treated group, volume and acidity measures were not different from those for saline control.

For the 12 saline treated rats, mean proteolytic activity was equivalent to a pepsin concentration of 1582.1 ug/ml; mean total pepsin output was 10657 micrograms. Compared to saline control, pepsin concentration and pepsin output for the rats in the CVT-1 treated group were very substantially reduced—by about 76 percent, and 81 percent, respectively. The reductions were statistically significant (p<0.05).

(B) Eighteen Hour Pylorus-Ligated Rat

After a 24 hour fast, rats were lightly anesthetized by methoxyflurane inhalation, and the standard Shay procedure (Shay et al. Gastroenterology 5:43, 1945) for ligation of the pylorus was performed. Immediately after pyloric ligation, rats were dosed by gavage with saline (control), CVT-1 125 mg/kg, or sucralfate 125 mg/kg; dose volumes 10 ml/kg.

Eighteen hours after pyloric ligation, surviving rats were sacrificed. Stomachs were removed and gastric lesion severity was graded according to a standard scale (0 to ±7). The abdomens of the dead rats were examined to verify that death had been due to perforation, i.e. severity grade 7.

| Grade | Description |
| --- | --- |
| 0 | No lesions |
| 1 | 5 lesions, all < 2.0 mm |
| 2 | 5 lesions, at least 1 lesion > 2.0 mm |
| 3 | 5-10 lesions, all < 2.0 mm |
| 4 | 5-10 lesions, at least 1 lesion > 2.0 mm |
| 5 | >10 lesions, all < 2.0 mm |
| 6 | >10 lesions, at least 1 lesion > 2.0 mm |
| 7 | Perforation |

In order to eliminate bias and reduce subjective variation, all ulcer grading in the study is performed in single-blind fashion by the same well-experienced grader.

Results are presented as means±standard errors of the means (n=12 per group). Statistical significance of differences between means were determined by analysis of variance and Newman-Keuls multiple comparisons test, or by the Chi Square test.

TABLE 7B

INHIBITION OF ULCER SEVERITY
IN THE 18 HOUR PYLORUS-LIGATED RAT

| Treatment | Ulcer Grade (scale 0 to 7) | Deaths (percent) |
| --- | --- | --- |
| Saline (control) | | |
| mean | 5.7 | 33.3 |
| ± sem | 0.4 | |
| CVT-1 | | |
| mean | 0.2* | 0.0* |
| ± sem | 0.2 | |
| reduction (%) | 97.0 | 100.0 |
| Sucralfate | | |
| mean | 0.8* | 0.0* |
| ± sem | 0.5 | |
| reduction (%) | 86.8 | 100.0 |

*significantly different from saline control, p < .05

Of the 12 saline treated rats, 4 rats died from perforating gastric ulcers before the end of the 18 hour test; thus mortality was 33 percent. The mean ulcer severity grade for the 12 saline treated rats was 5.7±0.4 (Table 2).

Compared to saline control, values for the rats in the CVT-1 treated group were remarkably reduced. Mortality was zero (P<0.05). Mean ulcer severity was almost zero (P<0.05).

Values for the rats in the sucralfate treated group were similar to those for the CVT-1 treated group. Mortality was zero (P<0.05). Mean ulcer severity was 0.8 (P<0.05).

(C) Ethanol-induced Gastric Injury

Antiulcer drugs with mucosal protective properties such as prostaglandins and sucralfate are effective in preventing the necrotizing action of ethanol on the gastric mucosa (Robert et al Gastroenterology 77:433, 1979). This test shows whether sulfated polysaccharides such as CVT-1 exhibit such cytoprotective action against absolute ethanol-induced injury.

After a 24 hour fast, rats were dosed by gavage with saline (control), CVT-1 125 mg/kg, or sucralfate 125 mg/kg; dose volumes 10 ml/kg. Thirty minutes after treatment with test agents, rats were dosed by gavage with absolute ethanol, 1.0 ml per rat.

One hour after ethanol, rats were sacrificed. Stomachs were removed and examined for the presence or absence of gastric lesions. For each stomach the gastric lesion severity score was the sum of the lengths (millimeters) of all lesions.

Results are presented as means±standard errors of the means (n=12 per group). Statistical significance of differences between means were determined by analysis of variance and Newman-Keuls multiple comparisons test.

TABLE 7C

INHIBITION OF ULCER SEVERITY
IN THE ETHANOL-INDUCED GASTRIC LESION MODEL

| Treatment | Ulcer Score |
| --- | --- |
| Saline (control) | |
| mean | 69.5 |
| ± sem | 3.9 |
| CVT-1 | |
| mean | 23.1* |
| ± sem | 4.4 |
| reduction (%) | 66.8 |
| Sucralfate | |
| mean | 33.2* |
| ± sem | 3.4 |
| reduction (%) | 52.2 |

*significantly different from saline control, p < .05

For the 12 saline treated rats, the mean ulcer score was 69.5±3.9.

Compared to saline control values for the rats in the CVT-1 treated group were very appreciably reduced. The mean ulcer score was 23.1±4.4, representing a reduction of about 67 percent (P<0.05).

Values for the rats in the sucralfate treated group were similar to those for the CVT-1 treated group. The mean ulcer score was 33.2±3.4, representing a reduction of about 52 percent (P<0.05).

(D) Aspirin-induced Gastric Ulcer Model

The major adverse effects associated with non steroidal anti-inflammatory drugs (NSAIDs) such as aspirin are gastric bleeding, erosions and ulcerations. This test shows antiulcer activity of CVT-1 against aspirin.

After a 24 hour fast, rats were dosed by gavage with aspirin suspension (2.00 grams/100 ml water plus 0.1% Tween 80; dose volume: 10 ml/kilogram). Thirty minutes after aspirin, rats were dosed by gavage with saline (control), CVT-1 125 mg/kg, or sucralfate 125 mg/kg; dose volumes 10 ml/kg.

Two hours after aspirin, rats were sacrificed. Stomachs were removed and examined with the aid of a magnifier (10×) for the presence or absence of gastric lesions.

Results are presented as means±standard errors of the means (n=15 per group). Statistical significance of differences between means were determined by analysis of variance and Newman-Keuls multiple comparisons test.

TABLE 7D

INHIBITION OF ULCER SEVERITY
IN THE ASPIRIN-INDUCED GASTRIC LESION MODEL

| Treatment | Ulcer Incidence (Percent of population having gastric lesions) |
|---|---|
| Saline (control) | |
| mean | 93.3 |
| CVT-1 | |
| mean | 80.0 |
| reduction (%) | 14.3 |
| Sucralfate | |
| mean | 46.7* |
| reduction (%) | 49.9 |

*significantly different from saline control, p < .05

Aspirin-induced gastric lesions were graded on an all or none basis (ulcers present or ulcers absent). Of the 15 saline treated rats, 14 had ulcers (93.3 percent).

Of the 15 CVT-1 treated rats, 12 had ulcers (80.3 percent). Compared to the saline control value, 80.3 percent represents a reduction of about 14 percent. p Of the 15 sucralfate treated rats, 7 had ulcers (46.7 percent). Compared to the saline control value, 46.7 percent represents a reduction of about 50 percent (P<0.05).

It is suggested that the dosage of CVT-1 must be increased to show activity in the asprin-induced gastric ulcer model.

What is claimed is:

1. A composition for treating gastric or duodenal ulcers comprising an effective amount of a very high molecular weight sulfated polysaccharide having a sulfate to monomer ratio of from 1.0 to about 3.0, containing less that about 5.0 wt. percent of sulfated polysaccharides having molecular weight less than 75,000 Daltons, and containing less than about 0.5 weight percent of free sulfates.

2. The composition of claim 1 wherein the effective amount of a high molecular weight sulfated polysaccharide is from about 10 mg to about 5000 mg.

3. The composition of claim 1 wherein the effective amount of a high molecular weight sulfated polysaccharide is administered along with one or more pharmaceutical excipients in a pharmaceutical dosage form selected from the group consisting of a tablet, capsule, liquid, or powder.

* * * * *